(12) United States Patent
McGregor

(10) Patent No.: US 7,727,256 B2
(45) Date of Patent: Jun. 1, 2010

(54) GRASPER ASSEMBLY

(75) Inventor: Robert McGregor, Chino Hills, CA (US)

(73) Assignee: Arthrex, Inc., Naples, FL (US)

( * ) Notice: Subject to any disclaimer, the term of this patent is extended or adjusted under 35 U.S.C. 154(b) by 719 days.

(21) Appl. No.: 11/235,258

(22) Filed: Sep. 26, 2005

(65) Prior Publication Data

US 2006/0069407 A1    Mar. 30, 2006

Related U.S. Application Data

(60) Provisional application No. 60/613,158, filed on Sep. 24, 2004.

(51) Int. Cl.
*A61B 17/00* (2006.01)

(52) U.S. Cl. ..................................... 606/208

(58) Field of Classification Search ......... 606/205–208; 81/315, 317–320, 324, 329, 338, 385, 394, 81/391; 24/506, 517
See application file for complete search history.

(56) References Cited

U.S. PATENT DOCUMENTS

| 382,712 | A | 5/1888 | Marr |
|---|---|---|---|
| 2,427,128 | A | 9/1947 | Ettinger |
| 2,439,785 | A | 4/1948 | Feitl et al. |
| 3,470,872 | A | 10/1969 | Grieshaber |
| 4,611,595 | A | 9/1986 | Klieman et al. |
| 4,813,407 | A | 3/1989 | Vogen |
| 4,896,661 | A | 1/1990 | Bogert et al. |
| 5,122,130 | A | 6/1992 | Keller |
| 5,176,702 | A * | 1/1993 | Bales et al. ............. 606/208 |
| 5,209,747 | A | 5/1993 | Knoepfler |
| 5,286,255 | A | 2/1994 | Weber |
| 5,314,424 | A | 5/1994 | Nicholas |
| 5,336,230 | A | 8/1994 | Leichtling et al. |
| 5,342,391 | A | 8/1994 | Foshee et al. |
| D350,606 | S | 9/1994 | Koros et al. |
| 5,366,467 | A | 11/1994 | Lynch et al. |

(Continued)

OTHER PUBLICATIONS

1990 Concept, Inc. Orthopaedic Products Catalog cover page and p. 55, Shutt Precision Instruments Hook Punch Forceps Styles.

(Continued)

*Primary Examiner*—Todd E Manahan
*Assistant Examiner*—Eric Blatt
(74) *Attorney, Agent, or Firm*—Carlson Gaskey & Olds PC

(57) ABSTRACT

The surgical instrument includes a shaft having a distal end portion and a proximal end portion; an operative device is disposed on the distal end portion. A hand mechanism has a first handle and a second handle and is disposed on the proximal end portion. Movement of the second handle relative to the first handle actuates the operative device. A ratchet, attached to the second handle, locks the operative device and moves with the second handle. The ratchet is pivotally attached to the second handle and pivots between a locked position and an unlocked position. A biasing device biases the ratchet toward the locked position and a release mechanism for moves the ratchet from the locked position. At least one of the release mechanism and the ratchet has a feature permitting relative movement between the release mechanism and the ratchet.

31 Claims, 5 Drawing Sheets

U.S. PATENT DOCUMENTS

| | | |
|---|---|---|
| 5,483,952 A | 1/1996 | Aranyi |
| 5,578,032 A | 11/1996 | Lalonde |
| 5,613,977 A * | 3/1997 | Weber et al. ............... 606/170 |
| 5,626,608 A | 5/1997 | Cuny et al. |
| 5,704,925 A | 1/1998 | Otten et al. |
| 5,728,121 A | 3/1998 | Bimbo et al. |
| 5,951,577 A | 9/1999 | Mayenberger et al. |
| 5,989,277 A | 11/1999 | LeMaire, III et al. |
| 6,116,124 A * | 9/2000 | Ping ........................... 81/385 |
| 6,117,158 A | 9/2000 | Measamer et al. |
| 6,139,563 A | 10/2000 | Cosgrove, III et al. |
| 6,620,184 B2 | 9/2003 | de Laforcade et al. |
| 6,626,929 B1 | 9/2003 | Bannerman |
| 6,643,935 B1 * | 11/2003 | Lowe et al. .................... 30/142 |
| 2006/0149315 A1 * | 7/2006 | Kebel et al. ................. 606/205 |

OTHER PUBLICATIONS

1990 Concept, Inc. Orthopaedic Products Price List, Effective Mar. 1, 1990 cover page and p. 5.

Two sheets containing sketches of the Shutt-Concept Grasper, P/N 11.1001.

* cited by examiner

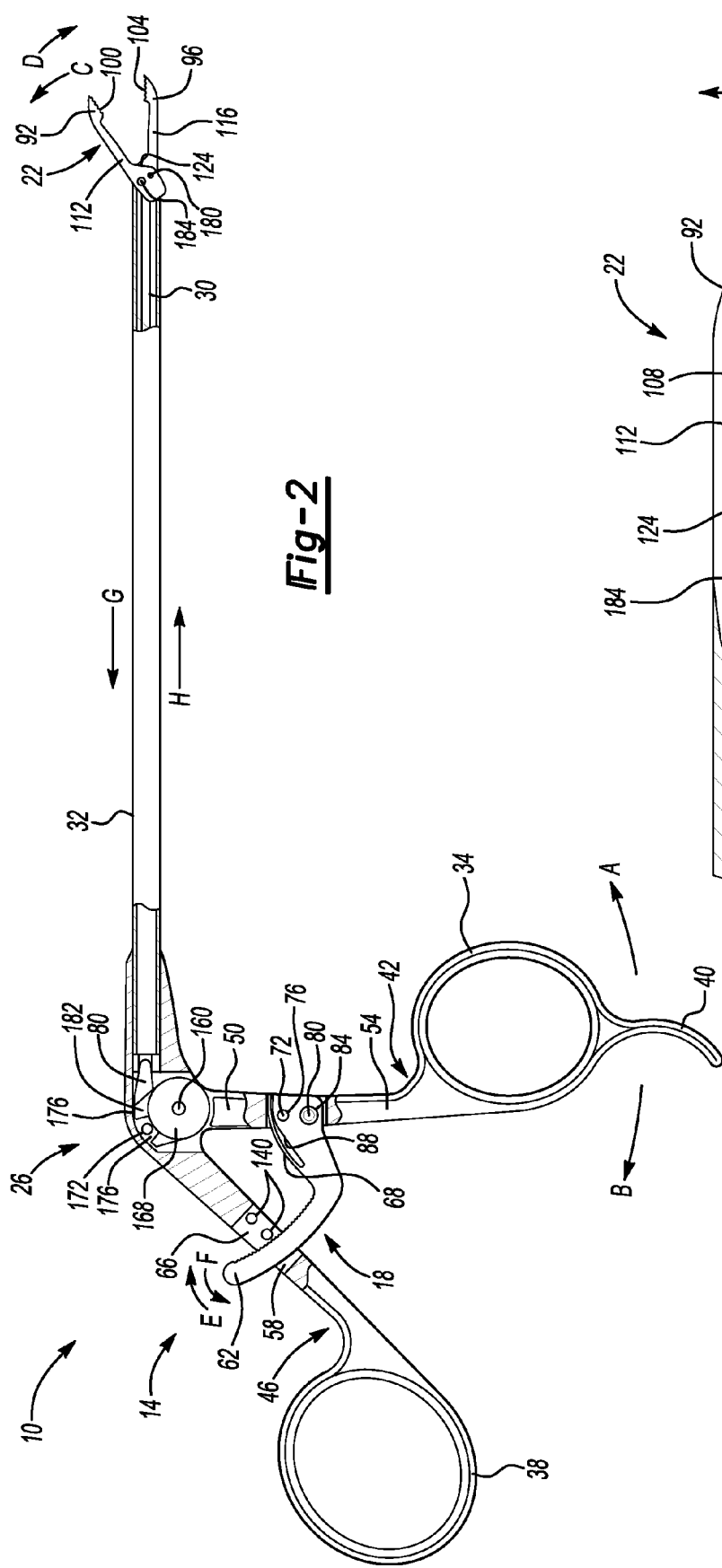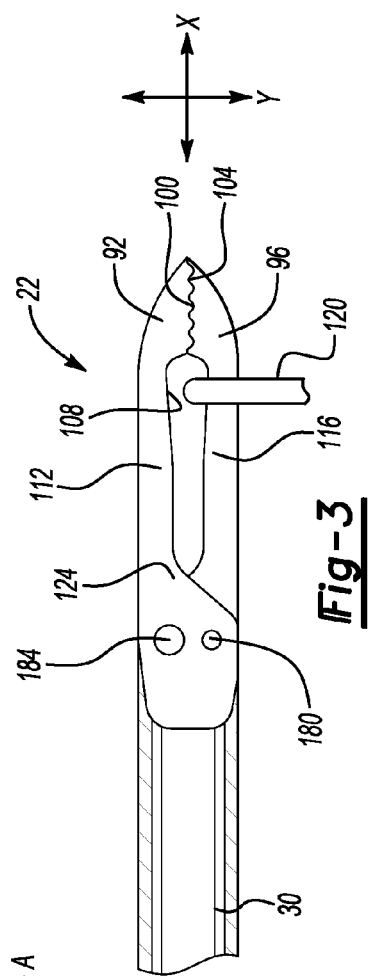

GRASPER ASSEMBLY

This nonprovisional application claims priority to U.S. Provisional Application No. 60/613,158, filed on Sep. 24, 2004.

BACKGROUND OF THE INVENTION

This invention relates to an endoscopic surgical instrument.

A surgical instrument, such as a clamp or suture retriever, may have jaws, a handle and a ratchet. Operation of the handle opens and closes the instrument's jaws, which are used to hold tissue or retrieve a suture. The ratchet allows the jaws to be locked in position once the ratchet is engaged. Generally, these instruments have a trigger that engages and disengages the ratchet. Consequently, a surgeon using the instrument must perform a two step process to operate the ratchet. First, the jaws of the instrument are opened or closed to a desired position. Second, the ratchet is engaged to lock the jaws in this position. It is desirable to simplify operation of this type of instrument.

Some devices of this type locate the trigger for actuating the ratchet on a finger loop of one of the handles. Hence, to operate the ratchet, a surgeon must move his finger from a position on the back part of the loop to the front part of the loop, where the trigger for the ratchet is located. Accordingly, the surgeon must hold his finger out to release the ratchet and then move the handles to operate the jaw. When closing the jaws of the instrument, the surgeon's hand must close while one of his fingers is held out to keep the ratchet released. This movement is awkward.

Also, the jaws of the instrument may have teeth to grasp tissue or a suture. However, there may be instances where it is desirable to pull on a suture without holding the suture in place. Accordingly, a need exists for a jaw that permits this freedom of movement.

SUMMARY OF THE INVENTION

Like existing surgical instruments, the present invention has handles, a ratchet, and jaws. The handles have a first handle and a second handle that operate in a scissor-like fashion to open and close the jaws. The ratchet is used to lock the jaws at a desired position.

In contrast to existing handles, the surgical instrument engages and disengages the ratchet by movement of one of the handles. Accordingly, opening of the handles opens the jaws and locks the jaws in place. Closing of the handles closes the jaws and simultaneously locks the jaws in place. Hence, the inventive instrument automatically engages and disengages the ratchet, thereby facilitating the locking and unlocking of the ratchet. In addition, the locking and unlocking of the instrument is in the same direction at the movement of the handle. Operation of the instrument is greatly facilitated.

The surgical instrument includes a shaft having a distal end portion and a proximal end portion; an operative device is disposed on the distal end portion. A hand mechanism has a first handle and a second handle and is disposed on the proximal end portion. Movement of the second handle relative to the first handle actuates the operative device. A ratchet, attached to the second handle, locks the operative device and moves with the second handle. The ratchet is pivotally attached to the second handle and pivots between a locked position and an unlocked position. A biasing device biases the ratchet toward the locked position and a release mechanism for moves the ratchet from the locked position. At least one of the release mechanism and the ratchet has a feature permitting relative movement between the release mechanism and the ratchet.

BRIEF DESCRIPTION OF THE DRAWINGS

The various features and advantages of this invention will become apparent to those skilled in the art from the following detailed description of the currently preferred embodiment. The drawings that accompany the detailed description can be briefly described as follows:

FIG. 2 illustrates an exposed cross-section of the instrument of FIG. 1, highlighting the features of the handle assembly, ratchet assembly and jaw assembly.

FIG. 3 illustrates a close up view of the jaw assembly of FIG. 2 with first jaw portion and second jaw portion closed to form an eyelet.

DETAILED DESCRIPTION OF THE PREFERRED EMBODIMENT

Figure 1:
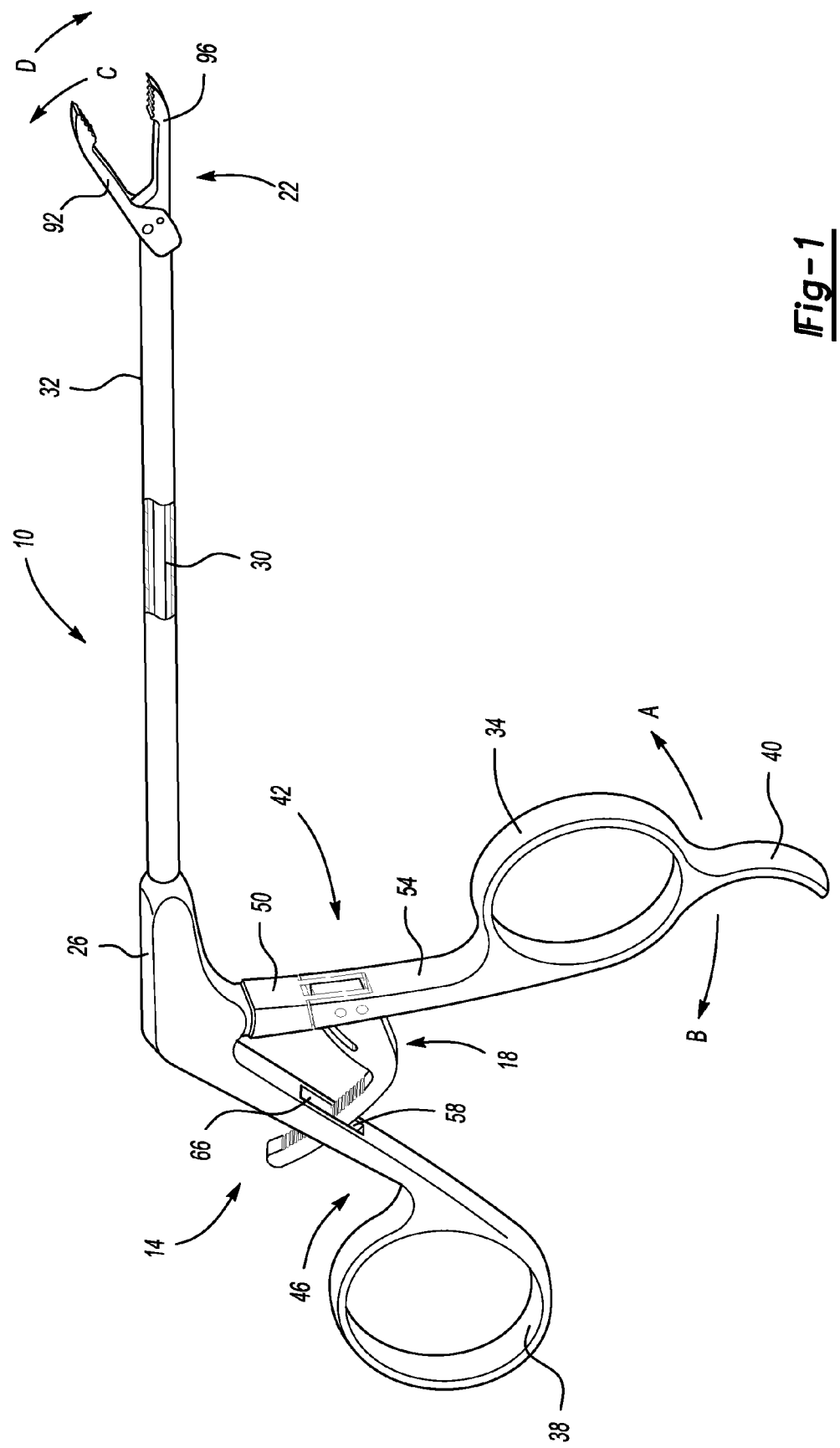
FIG. 1 illustrates a view of the surgical instrument, including handle assembly, ratchet assembly and jaw assembly.

FIG. 1 illustrates a perspective view of surgical instrument 10. Here, instrument 10 has handle assembly 14, ratchet assembly 18, and jaw assembly 22. Body assembly 26 connects an operative device, such as a jaw assembly 22, to handle assembly 14 through transmitting rod 30. The jaw assembly 22 connects to the distal end of the transmitting rod 30 and the handle assembly 14 connects to the proximal end. Handle assembly 14, or other such hand mechanism, has first handle 42 and second handle 46. Jaw assembly 22 has first jaw portion 92 and second jaw portion 96, which are pivotally connected at jaw pivot 180. As will be explained in further detail, opening of first handle 42 in the direction of arrow A causes first jaw portion 92 to open relative to second jaw portion 96 in the direction of arrow C. Conversely, closing of first handle 42 in the direction of arrow B causes first jaw portion 92 to close in the direction of arrow D relative to second jaw portion 96.

Inventive instrument 10 has locking mechanism, such as a ratchet assembly 18, that locks first handle 42 relative to second handle 46 to thereby lock first jaw portion 92 relative to second jaw portion 96 at any position between a completely closed position as shown in FIG. 3 to a completely open position. When first handle 42 is moved in either the direction of arrow A or arrow B, ratchet assembly 18 is disengaged. When movement is stopped, ratchet assembly 18 is automatically engaged. Hence, instrument 10 automatically operates to lock jaw assembly 22 without additional effort to engage or disengage ratchet assembly 18.

As shown in FIG. 3, jaw assembly 22 has first jaw portion 92 and second jaw portion 96. First jaw portion 92 has first teeth section 100 located at the distal end of transmitting rod 30 and back portion 124 located more proximal to transmitting rod 30. Between first teeth section 100 and back portion 124 is provided first gap portion 112, a length of first jaw portion 92 that has no teeth and is provided with a gap. Similarly, second jaw portion 96 has second teeth section 104, second gap portion 116, and back portion 124. When first jaw portion 92 is closed relative to second jaw portion 96, an eyelet 108 is formed by first gap portion 112 and second gap portion 116 between teeth sections 100, 104 and back portion 124. Eyelet 108 is sized larger than suture 120 so that suture 120 may slide through eyelet 108, thereby permitting movement through eyelet 108 of suture 120 along the Y axis but preventing movement of suture 120 along the X axis, as shown.

The operation of instrument 10 will now be explained in detail with reference to FIGS. 2 and 4-8. Instrument 10 is shown in partial cross-section in FIG. 2. As shown, jaw assembly 22 is linked to handle assembly 14 by transmitting rod 30 housed within a shaft, such as transmitting rod housing 32. Transmitting rod 30 is linked to first jaw portion 92 at jaw link 184. Handle assembly 14 has first handle 42 and second handle 46, which is formed as part of body assembly 26. At body assembly 26, first handle 42 is pivotally connected to second handle 46 through handle pivot 160. Accordingly, first handle 42 may pivot relative to the second handle 46 in the direction of either arrow A or arrow B. Transmitting rod 30 is linked to first handle 42 at handle link 182. Therefore, movement of first handle 42 in the direction of arrow A causes transmitting rod 30 to move in the direction of arrow G. First jaw portion 92 is pulled in the same direction and pivots first jaw portion 92 relative to second jaw portion 96 on jaw pivot 180. First jaw portion 92 moves in the direction of arrow C relative to second jaw portion 96. Movement of first handle 42 in the direction of arrow B causes transmitting rod 30 to move in the direction of arrow H, thereby pivoting first jaw portion 92 to close in the direction of arrow D. It should be noted that first handle 42 is provided with well 176 that engages stop 172 on body assembly 26. In this way, first handle 42 is prevented from closing or opening jaw assembly 22 beyond predetermined points to safeguard jaw assembly 22.

Ratchet assembly 18 is provided on instrument 10 to lock jaw assembly 22 in a particular position. Ratchet assembly 18 has ratchet arm 62, which is pivotally linked to first handle 42 at pivot pin 72 through pivot hole 76 on ratchet arm 62. Accordingly, ratchet arm 62 pivots in the direction of arrow E or in the direction of arrow F, as shown in FIG. 2. Ratchet arm 62 is provided with spring 68, a leaf spring, that engages first handle top portion 50. Spring 68 is biased in the direction of arrow E so that ratchet arm 62 is engaged to an engagement plate 66 of second handle 46. The engagement plate 66 is mounted to second handle 46 by pins 140. When first handle 42 and second handle 46 are not moved relative to each other, spring 68 biases ratchet arm 62 into engagement with the engagement plate 66 so that first handle 42 is locked in position relative to second handle 46 and accordingly first jaw portion 92 is locked in position relative to second jaw portion 96.

Figure 4:
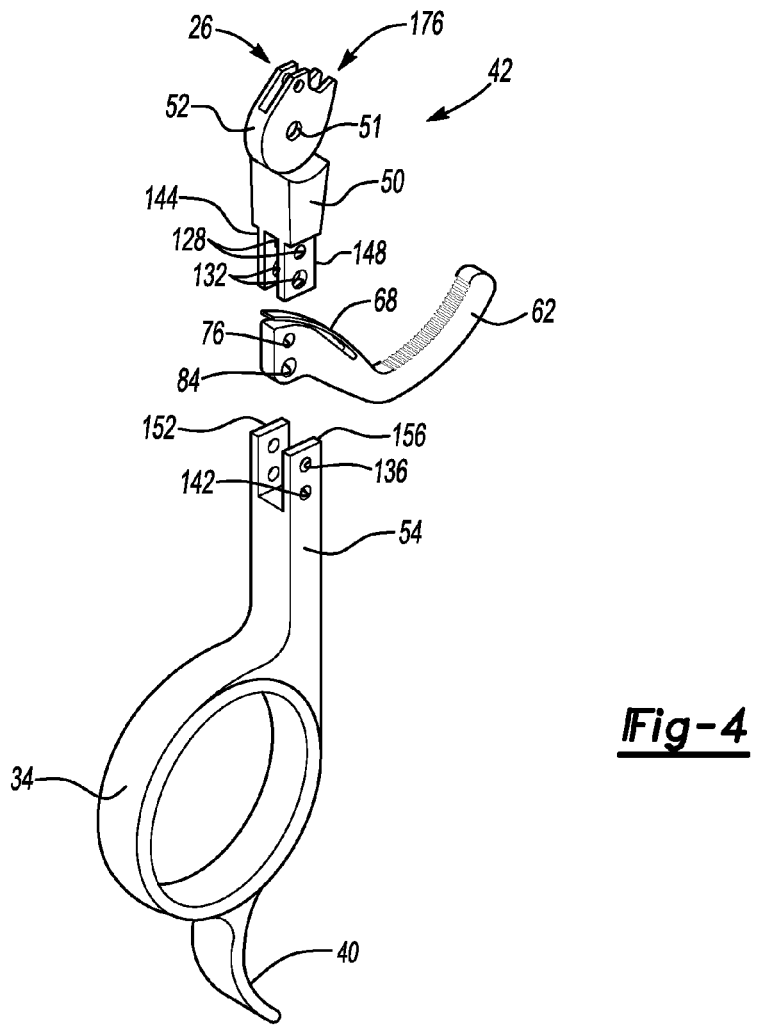
FIG. 4 illustrates an exploded view of one of the handles of the instrument of FIGS. 1-2, highlighting the ratchet assembly.

As shown in FIG. 4, first handle 42 comprises first handle top portion 50 and first handle bottom portion 54. First handle top portion 50 has pivot base 52, which is received on handle pivot 160 of body assembly 26 through pivot hole 51. First handle top portion 50 further has first upper portion leg 144 and second upper portion leg 148. Each leg 144, 148 is provided with first upper holes 128 and second upper holes 132. First upper portion leg 144 and second upper portion leg 148 are sized to receive ratchet arm 62 so that spring 68 is nestled between first upper portion leg 144 and second upper portion leg 148 against first handle top portion 50. Also, ratchet arm 62 has pivot hole 76 and release hole 84, which are arranged to align with first upper hole 128 and second upper hole 132, respectively, when ratchet arm 62 is received between first upper portion leg 144 and second upper portion leg 148.

First handle bottom portion 54 has finger loop 34 sized to receive a finger as well as support shoulder 40, which is shaped to receive another finger. First handle bottom portion 54 further has first lower portion leg 152 and second lower portion leg 156. Each leg 152, 156 has first lower holes 136 and second lower holes 142. First lower portion leg 152 and second lower portion leg 156 are sized to receive first upper portion leg 144 and second upper portion leg 148. Accordingly, when first handle 42 is fully assembled, as shown in FIG. 2, first upper holes 128 align with pivot hole 76 and first lower holes 136 while second upper holes 132 align with release hole 84 and second lower holes 142.

When the holes are aligned, pivot pin 72 is placed through first lower holes 136, first upper holes 128, and pivot hole 76. Release pin 80 is placed through second lower holes 142, second upper holes 132, and release hole 84. Pivot pin 72 and release pin 80, or similar feature, are capped at each end to retain their position within these holes.

The size of the holes relative to each other and to pins 72 and 80 assist ratchet assembly 18 in its engagement and disengagement with the engagement plate 66. Referring again to FIG. 4, first lower holes 136 and second lower holes 142 have about the same diameter as pivot pin 72 and release pin 80, say 0.062 inches. First upper holes 128 and second upper holes 132 of first handle top portion 50 have different diameters. For example, first upper holes 128 may have a diameter of 0.0620 inches while second upper holes 132 may have a larger diameter, say 0.072 inches. Also, ratchet arm 62 has holes of differing sizes. Pivot hole 76 has a diameter of, say 0.0620 inches. Release hole 84 has a diameter, say 0.072 inches. Accordingly, because of the size of pivot pin 72 and release pin 80, ratchet arm 62 may not only pivot on pivot 72 but has some freedom of movement to move about pivot pin 72 and release pin 80, particularly release pin 80, which is in this case about 0.01 inches smaller than release hole 84.

Figure 5:
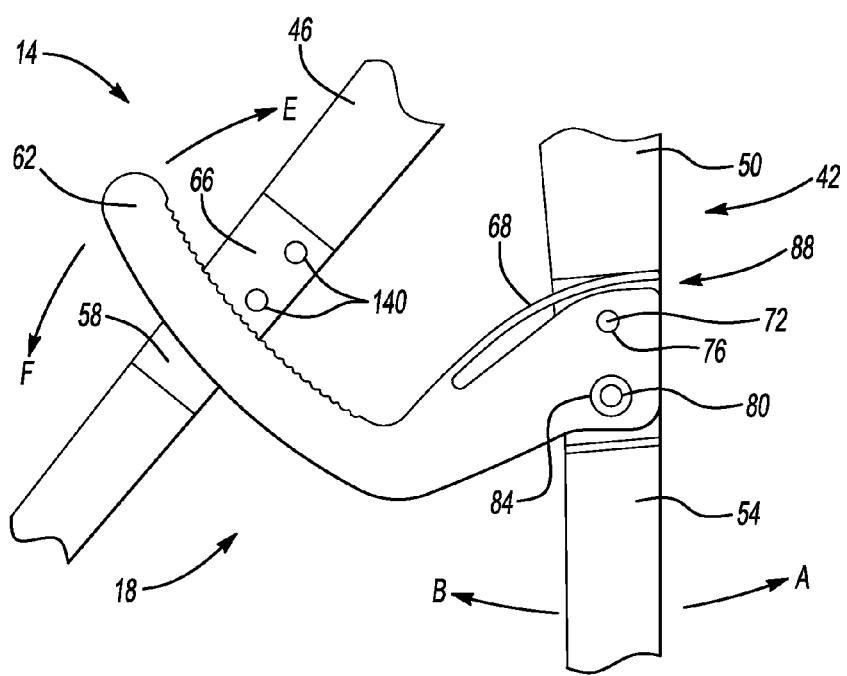
FIG. 5 illustrates the ratchet assembly of FIG. 4 in a locked position.
Figure 6:
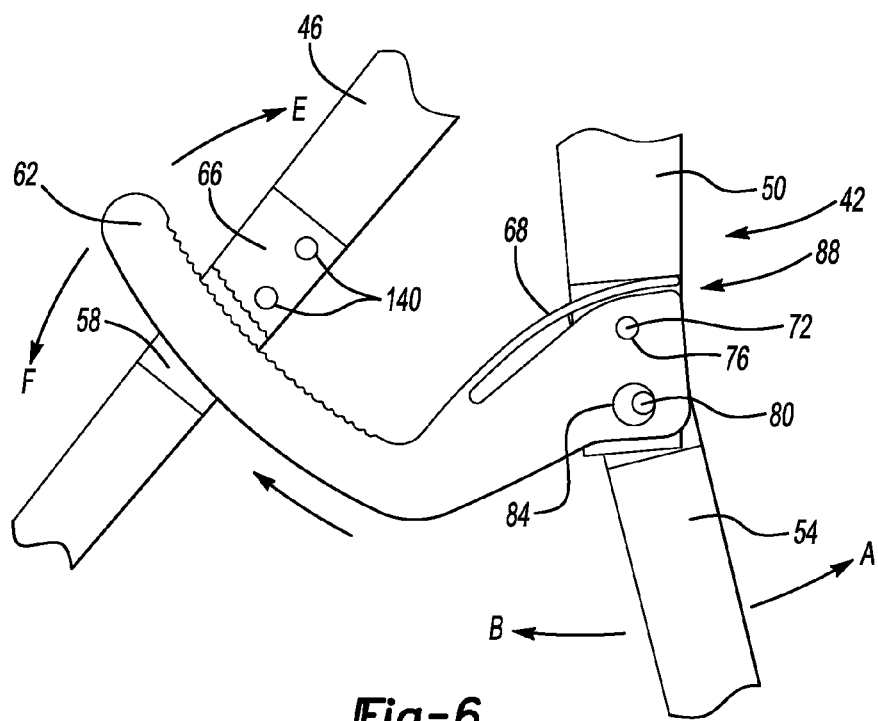
FIG. 6 illustrates the ratchet assembly of FIG. 4 in an unlocked position.

The functioning of ratchet assembly 18 with respect to these holes will now be explained with reference to FIG. 5-8. FIG. 5 illustrates a close-up view of handle assembly 14 in cross-section. As shown, ratchet arm 62 is mounted to pivot pin 72 by pivot hole 76 and pivots about pivot pin 72 in the direction of arrow E or F. In addition, release pin 80 is shown mounted through release hole 84 of ratchet arm 62. As shown, there is space between release pin 80 and release hole 84 so that release pin 80 does not touch the sides of release hole 84 in the position shown in FIG. 5, which is the position where no force is applied to first handle 42. In this position, the ratchet arm 62 is decoupled from movement with the first handle bottom portion 54. Ratchet arm 62 has spring 68, which engages first handle top portion 50. Spring 68 is biased so that ratchet arm 62 engages the engagement plate 66 as shown. In addition, there is a ratchet opening 58 provided that permits movement of ratchet arm 62 in the direction of arrow F away from engagement with the engagement plate 66. As shown in FIG. 6, when pressure is applied to first handle bottom portion 54, release pin 80 contacts release hole 84 in the direction of arrow A overcoming the bias of spring 68. Thus, first handle bottom portion 54 acts as a release mechanism for the ratchet arm 62. In this position, the ratchet arm 62 is coupled with the first handle bottom portion 54 thereby linking movement of the first handle bottom portion 54 with the ratchet arm 62. As a consequence, ratchet arm 62 pivots about pivot pin 72 in the direction of arrow F into ratchet opening 58. Hence, ratchet arm 62 is disengaged from the engagement plate 66. As a consequence, further movement of first handle bottom portion 54 in the direction of arrow A is permitted and causes ratchet arm 62 to move generally in the same direction. First jaw portion 92 may then open relative to second jaw portion 96 in the direction of arrow C. When force is no longer applied to first handle bottom portion 54, then handle assembly 14 releases pressure on spring 68, allowing spring 68 to bias ratchet arm 62 into engagement with the engagement plate 66 as shown in FIG. 5.

Figure 7:
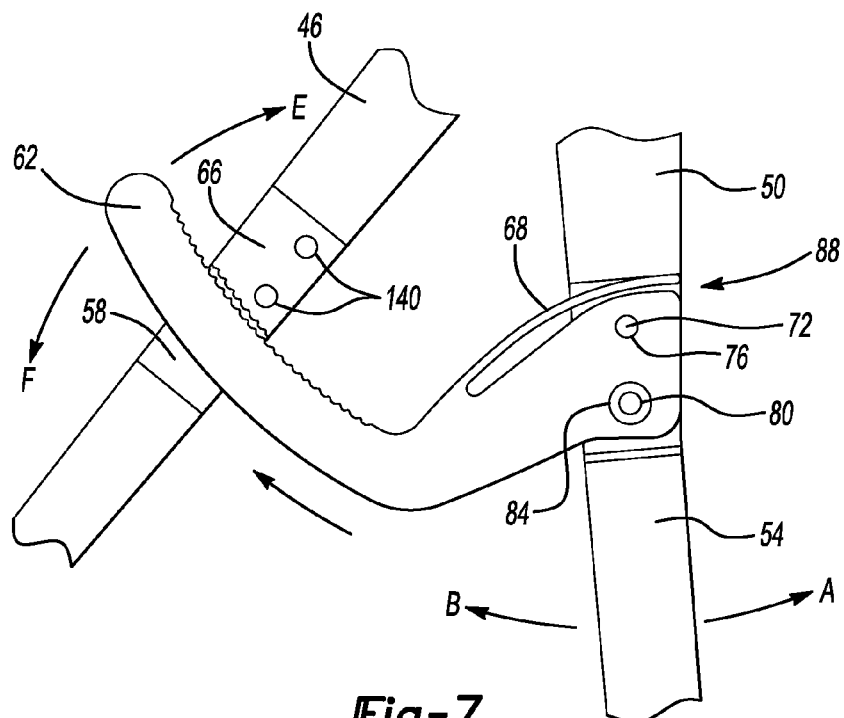
FIG. 7 illustrates the ratchet assembly of FIG. 4 in another unlocked position.
Figure 8:
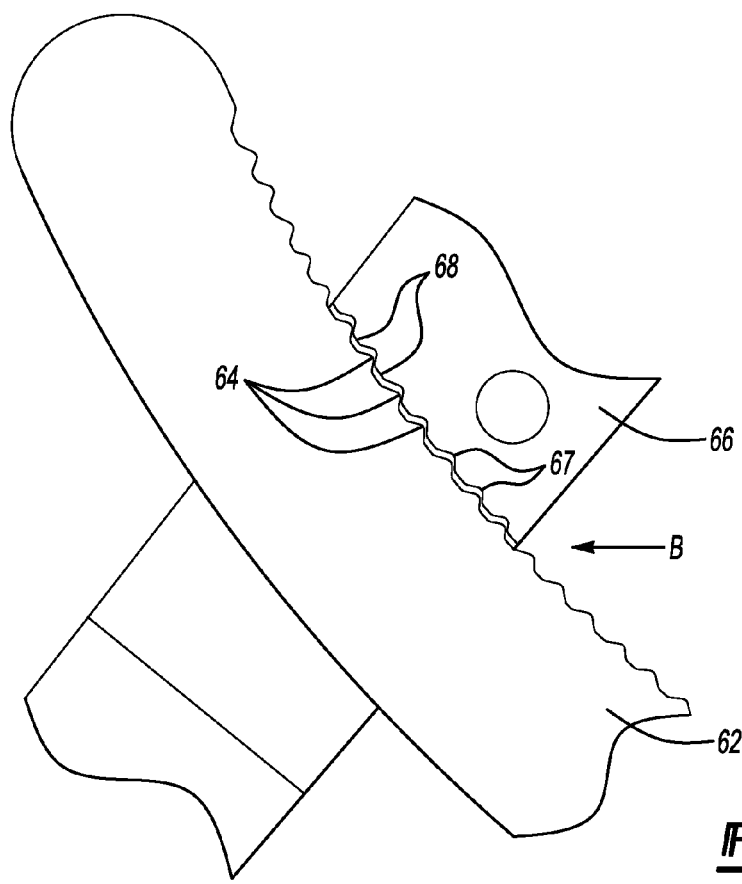
FIG. 8 illustrates in detail the unlocked position of FIG. 7.

On the other hand, as shown in FIG. 7, if a surgeon wishes to close jaw assembly 22, first handle bottom portion 54 is moved back in the direction of arrow B. Movement in this direction compresses spring 68. This pressure on spring 68 is released as ratchet arm 62 is moved back generally in the direction of arrow B. Ratchet teeth 64 are angled relative to the engagement plate teeth 68 so as to permit ratchet arm 62 to slide across engagement plate teeth 68 in the direction of arrow B as shown in FIG. 8. It should be noted that here, release pin 80 does not contact the side of release hole 84 because spring 68 will cause ratchet arm 62 to slide across the engagement plate teeth 68 and engagement plate detents 67 without engagement until pressure on first handle bottom portion 54 is stopped. Once stopped, ratchet arm 62 engages the engagement plate 66 by engaging ratchet teeth 64 to the engagement plate teeth 68 and engagement plate detents.

Figure 9:
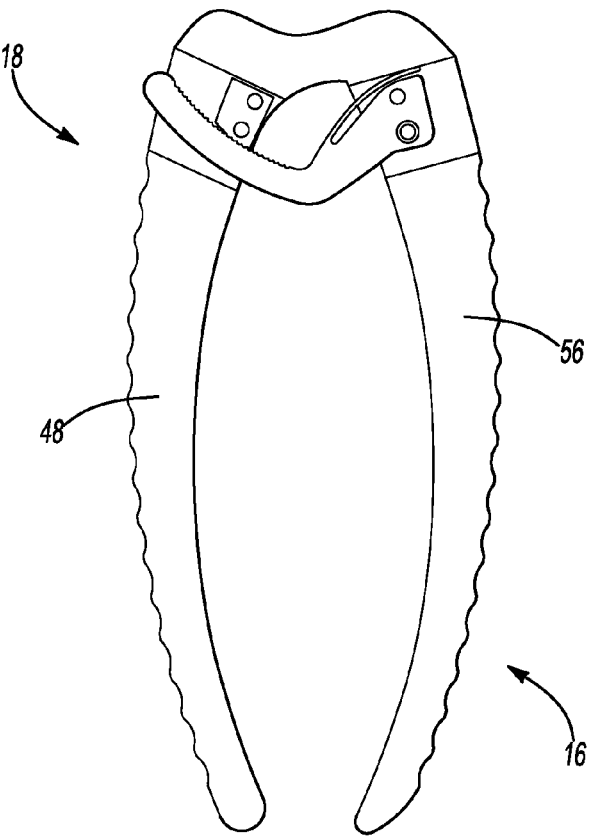
FIG. 9 illustrates an exposed section of the ratchet assembly incorporated into a wishbone handle design.

In addition to the heretofore described handles 14 having ring-type profiles, instrument 10 may utilize a set of wishbone type handles 16 as shown in FIG. 9. The ratchet assembly 18 interfaces with the wishbone handles 16 in the same manner as the ring handles 14. Movement of a first wishbone handle bottom portion 56 relative to a second wishbone handle bottom portion 48 actuates the ratchet assembly 18.

Although a preferred embodiment of this invention has been disclosed, a worker of ordinary skill in the art might recognize that certain modifications are possible that would come within the scope of this invention. For that reason, the following claims should be studied to determine the true scope of protection given for this invention.

What is claimed is:

1. A surgical instrument comprising:
 a shaft having a distal end portion and a proximal end portion;
 an operative device disposed on said distal end portion;
 a hand mechanism to operate said operative device on said proximal end portion, said hand mechanism having a first handle and a second handle, wherein movement of said second handle relative to said first handle in a first direction or a second direction actuates said operative device;
 a ratchet for locking said operative device, said ratchet carried by said second handle and moveable with said second handle, said ratchet moveable between a locked position and an unlocked position; and
 a release mechanism for moving said ratchet between said locked position and said unlocked position, at least one of said release mechanism and said ratchet having a feature permitting relative movement between said release mechanism and said ratchet when said ratchet is in said locked postion.

2. The surgical instrument of claim 1, wherein said ratchet is pivotally secure to said release mechanism, said feature permitting said ratchet to pivot relative to said release mechanism.

3. The surgical instrument of claim 2, wherein said release mechanism is configured to pivot said ratchet between said locked position and said unlocked position.

4. A surgical instrument comprising:
 a shaft having a distal end portion and a proximal end portion;
 an operative device disposed on said distal end portion;
 a hand mechanism to operate said operative device on said proximal end portion, said hand mechanism having a first handle and a second handle, wherein movement of said second handle relative to said first handle in a first direction or a second direction actuates said operative device;
 a ratchet for locking said operative device, said ratchet carried by said second handle and moveable with said second handle, said ratchet moveable between a locked position and an unlocked position; and
 a release mechanism for moving said ratchet between said locked position and said unlocked position, at least one of said release mechanism and said ratchet having a feature permitting relative movement between said release mechanism and said ratchet, wherein said second handle comprises a first portion and a second portion, said first portion linked to said second portion by a handle pivot permitting said first portion to pivot relative to said second portion, said ratchet pivotally linked to at least one of said first portion and said second portion.

5. The surgical instrument of claim 1, wherein said feature creates a coupled condition and a decoupled condition, said release mechanism linked in movement with said ratchet in said coupled condition and said release mechanism free to move relative to said ratchet in said decoupled condition.

6. The surgical instrument of claim 1, wherein said feature comprises a pin disposed in a hole, said hole sized larger than said pin to permit relative movement between said release mechanism and said ratchet.

7. A surgical instrument comprising:
 a shaft having a distal end portion and a proximal end portion;
 an operative device disposed on said distal end portion;
 a hand mechanism to operate said operative device on said proximal end portion, said hand mechanism having a first handle and a second handle, wherein movement of said second handle relative to said first handle in a first direction or a second direction actuates said operative device;
 a ratchet for locking said operative device, said ratchet carried by said second handle and moveable with said second handle, said ratchet moveable between a locked position and an unlocked position; and
 a release mechanism for moving said ratchet between said locked position and said unlocked position, at least one of said release mechanism and said ratchet having a feature permitting relative movement between said release mechanism and said ratchet, wherein said feature comprises a pin disposed in a hole, said hole sized larger than said pin to permit relative movement between said release mechanism and said ratchet, wherein said hole is on said ratchet and said pin is on said release mechanism.

8. The surgical instrument of claim 1, wherein said ratchet is pivotally connected to said second handle about a ratchet pivot.

9. The surgical instrument of claim 8, wherein said ratchet is located further from said ratchet pivot than said feature.

10. The surgical instrument of claim 8, wherein said ratchet pivot is moveable with said second handle.

11. A surgical instrument comprising:
a shaft having an operative device disposed on a distal end portion of said shaft and a first handle disposed on a proximal end portion of said shaft;
a second handle disposed on said proximal end portion of said shaft wherein movement of said second handle relative to said first handle actuates said operative device;
a locking mechanism for locking said operative device, said locking mechanism caffied by at least one of said first handle and said second handle and moveable between a locked position and an unlocked position; and
a release mechanism for moving said locking mechanism between said locked position and said unlocked position, said release mechanism having a coupled condition linking movement of said release mechanism to said locking mechanism and a decoupled condition disassociating movement of said release mechanism from said locking mechanism, wherein said release mechanism is free to move to said decoupled condition from said coupled condition.

12. A surgical instrument comprising:
a shaft having an operative device disposed on a distal end portion of said shaft and a first handle disposed on a proximal end portion of said shaft;
a second handle disposed on said proximal end portion of said shaft wherein movement of said second handle relative to said first handle actuates said operative device;
a locking mechanism for locking said operative device, said locking mechanism carried by at least one of said first handle and said second handle and moveable between a locked position and an unlocked position; and
a release mechanism for moving said locking mechanism between said locked position and said unlocked position, said release mechanism having a coupled condition linking movement of said release mechanism to said locking mechanism and a decoupled condition disassociating movement of said release mechanism from said locking mechanism, wherein said release mechanism is free to move to said decoupled condition from said coupled condition, wherein said release mechanism is free to move between said coupled condition and said decoupled condition as said locking mechanism remains in said locked position.

13. The surgical instrument of claim 11, wherein said release mechanism is free to move relative to at least one of said first handle and said second handle.

14. The surgical instrument of claim 11, wherein said locking mechanism includes at least one tooth operative to engage at least one detent on at least one of said first handle and said second handle.

15. A surgical instrument comprising:
a shaft having an operative device disposed on a distal end portion of said shaft and a first handle disposed on a proximal end portion of said shaft;
a second handle disposed on said proximal end portion of said shaft wherein movement of said second handle relative to said first handle actuates said operative device;
a locking mechanism for locking said operative device, said locking mechanism caffied by at least one of said first handle and said second handle and moveable between a locked position and an unlocked position; and
a release mechanism for moving said locking mechanism between said locked position and said unlocked position, said release mechanism having a coupled condition linking movement of said release mechanism to said locking mechanism and a decoupled condition disassociating movement of said release mechanism from said locking mechanism, wherein said release mechanism is free to move to said decoupled condition from said coupled condition, wherein said locking mechanism includes at least one tooth operative to engage at least one detent on at least one of said first handle and said second handle, wherein said release mechanism is free to move between said coupled condition and said decoupled condition as said at least one tooth engages said at least one detent.

16. The surgical instrument of claim 11, including a biasing portion operative to bias said locking mechanism toward said locked position.

17. The surgical instrument of claim 16, wherein said biasing portion is a spring.

18. The surgical instrument of claim 16, wherein said locking mechanism assembly is pivotally connected to at least one of said first handle and said second handle at a locking mechanism pivot.

19. The surgical instrument of claim 18, wherein said release mechanism is further from said locking mechanism pivot point than said biasing portion.

20. A surgical instrument comprising:
a shaft having a distal end portion and a proximal end portion;
an operative device disposed on said distal end portion;
a hand mechanism to operate said operative device on said proximal end portion, said hand mechanism having a first handle and a second handle, wherein movement of said second handle relative to said first handle in a first direction or a second direction actuates said operative device;
a ratchet for locking said operative device, said ratchet pivotally attached to said second handle and moveable with said second handle, said ratchet pivotally moveable between a locked position and an unlocked position;
a biasing device operative to bias said ratchet toward said locked position; and
a release mechanism for moving said ratchet between said locked position and said unlocked position, at least one of said release mechanism and said ratchet having a feature permitting relative pivoting between said release mechanism and said ratchet, said release mechanism linked in movement with said biasing device.

21. A surgical instrument comprising:
a shaft having a distal end portion and a proximal end portion;
an operative device disposed on said distal end portion;
a hand mechanism to operate said operative device on said proximal end portion, said hand mechanism having a first handle and a second handle, wherein movement of said second handle relative to said first handle in a first direction or a second direction actuates said operative device;
a ratchet for locking said operative device, said ratchet pivotally attached to said second handle and moveable with said second handle, said ratchet pivotally moveable between a locked position and an unlocked position;
a biasing device operative to bias said ratchet toward said locked position; and
a release mechanism for moving said ratchet between said locked position and said unlocked position, at least one of said release mechanism and said ratchet having a feature permitting relative pivoting between said release mechanism and said ratchet, said release mechanism linked in movement with said biasing device, wherein said feature comprises a pin disposed in a hole, said hole sized larger than said pin to permit relative movement between said release mechanism and said ratchet, wherein said pin is on one of said ratchet and said release mechanism, and the hole is defined within the other of said ratchet and said release mechanism.

22. A surgical instrument comprising:
a shaft having a distal end portion and a proximal end portion;
an operative device disposed on said distal end portion;
a first handle and a second handle for operating said operative device on said proximal end portion;
a ratchet for locking said operative device, said ratchet carried by said first handle, said ratchet moveable between a locked position and an unlocked position; and
a handle bottom pivotably connected to said first handle, wherein movement of said handle bottom toward said second handle closes said operative device, limiting movement of said handle bottom toward said ratchet locks the operative device, and movement of said handle bottom away from said second handle unlocks said ratchet and opens said operative device.

23. The surgical instrument of claim 22, wherein said ratchet is pivotally linked to said handle bottom at a pivot that permits said ratchet to pivot relative to said handle bottom.

24. The surgical instrument of claim 23, wherein said ratchet pivots between said locked position and said unlocked position.

25. The surgical instrument of claim 22, wherein said ratchet creates a coupled condition and a decoupled condition, said handle bottom linked in movement with said ratchet in said coupled condition and said handle bottom free to move relative to said ratchet in said decoupled condition.

26. A method of actuating a surgical device having an operative device on a distal end and a plurality of handles to operate the operative device on a proximal end, comprising:
a) moving a first handle in a first direction relative a second handle to actuate the operative device on the distal end of the shaft, the first handle and the second handle on a proximal end of the shaft;
b) locking the operative device while maintaining the position of the first handle relative to the second handle; and
c) moving the first handle in a second direction opposite the first direction relative the second handle to unlock the operative device.

27. The method of claim 26 wherein said step b) includes engaging at least one ratchet tooth when locking the operative device.

28. The method of claim 26 wherein said step b) includes biasing the at least one ratchet tooth toward an engaged position.

29. The surgical instrument of claim 1, wherein said first handle and said second handle extend transversely from said shaft.

30. The surgical instrument of claim 1, wherein movement of said second handle relative to said first handle translates a rod relative to said shaft to actuate said operative device.

31. The surgical instrument of claim 1, wherein said ratchet is directly pivotally secured to said release mechanism.

* * * * *

UNITED STATES PATENT AND TRADEMARK OFFICE
CERTIFICATE OF CORRECTION

PATENT NO. : 7,727,256 B2  Page 1 of 1
APPLICATION NO. : 11/235258
DATED : June 1, 2010
INVENTOR(S) : Weber It is certified that error appears in the above-identified patent and that said Letters Patent is hereby corrected as shown below:

Title Page; item (75);

The "Inventor" section on the patent's front page should read as follows:

Robert McGregor Weber, Chino Hills, CA (US)

In the claims:

Claim 2, Column 5, line 65: "secure" should read as --secured--

Claim 11, Column 7, line 9: "caffied" should read as --carried--

Claim 15, Column 7, line 59: "caffied" should read as --carried--

Signed and Sealed this

Second Day of November, 2010

David J. Kappos
*Director of the United States Patent and Trademark Office*